United States Patent
Schulz et al.

(10) Patent No.: US 9,207,186 B2
(45) Date of Patent: Dec. 8, 2015

(54) METHOD AND ARRANGEMENT FOR MEASURING BLOWING STRUCTURES OF A PRESTRESSED DISC

(71) Applicant: SAINT-GOBAIN GLASS FRANCE, Courbevoie (FR)

(72) Inventors: Valentin Schulz, Aachen (DE); Lutz Hermanns, Moenchengladbach (DE); Lars Pape, Eschweiler (DE); Stephan Kremers, Heinsberg (DE)

(73) Assignee: SAINT-GOBAIN GLASS FRANCE, Courbevoie (FR)

( * ) Notice: Subject to any disclaimer, the term of this patent is extended or adjusted under 35 U.S.C. 154(b) by 0 days.

(21) Appl. No.: 14/380,245

(22) PCT Filed: Apr. 10, 2013

(86) PCT No.: PCT/EP2013/057469
§ 371 (c)(1),
(2) Date: Aug. 21, 2014

(87) PCT Pub. No.: WO2013/160105
PCT Pub. Date: Oct. 31, 2013

(65) Prior Publication Data
US 2015/0036120 A1   Feb. 5, 2015

(30) Foreign Application Priority Data
Apr. 23, 2012  (EP) .................................... 12165122

(51) Int. Cl.
*G01B 11/16*  (2006.01)
*G01N 21/88*  (2006.01)
(Continued)

(52) U.S. Cl.
CPC ............ *G01N 21/8806* (2013.01); *G01L 1/241* (2013.01); *G01N 21/896* (2013.01); *G01N 21/958* (2013.01); *G01N 33/386* (2013.01); *G01N 2021/8848* (2013.01)

(58) Field of Classification Search
CPC ................................. G01B 11/16; G01N 21/00
USPC ....................................... 356/35, 239.1, 239.7
See application file for complete search history.

(56) References Cited

U.S. PATENT DOCUMENTS

| | | | | |
|---|---|---|---|---|
| 4,655,589 A | * | 4/1987 | Cestaro | G01L 1/241 356/35 |
| 6,881,485 B2 | * | 4/2005 | Kato | C03B 27/0404 428/409 |
| 2002/0194872 A1 | * | 12/2002 | Kato | C03B 27/0404 65/114 |

FOREIGN PATENT DOCUMENTS

WO    2011/157815    12/2011

OTHER PUBLICATIONS

Castellini, P., et al. "Laser sheet scattered light method for industrial measurement of thickness residual stress distribution in flat tempered glass" *Optics and Lasers Engineering*, 50:5 (2012) 787-795.
(Continued)

*Primary Examiner* — Roy M Punnoose
(74) *Attorney, Agent, or Firm* — Steinfl & Bruno LLP

(57) ABSTRACT

A method for measuring blowing structures of a prestressed disc is described. The method has the steps of: (a) irradiating at least one analysis area of the disc with linearly polarized light from a radiation source at an angle of incidence and recording an image at least of the analysis area at an angle of observation using at least one detector, (b) supplying the image to an evaluation unit, and (c) using the evaluation unit to read a brightness profile along an analysis line on the image, to determine the local maxima and the local minima of the brightness profile, and to determine an intensity index by means of the difference between a brightness mean of the local maxima and a brightness mean of the local minima.

15 Claims, 6 Drawing Sheets

Figure 1:
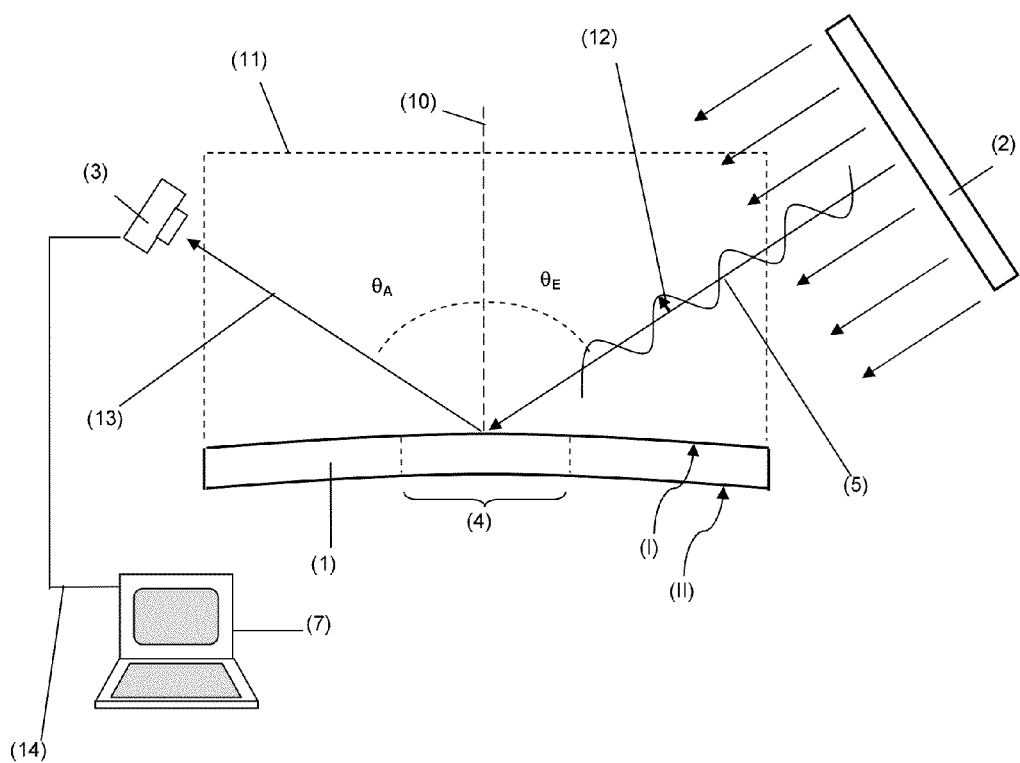

(51) Int. Cl.
*G01N 21/896* (2006.01)
*G01N 21/958* (2006.01)
*G01L 1/24* (2006.01)
*G01N 33/38* (2006.01)

(56) References Cited

OTHER PUBLICATIONS

Chagnon, P. "Optics for People Stuck in Traffic: Stress Patterns" *The Physics Teacher* 32 (1994) p. 166f.

PCT Written Opinion mailed on Aug. 20, 2013 for PCT/EP2013/057469 filed on Apr. 10, 2013 in the name of Saint-Gobain Glass France.

"PS-100 Polarimeter/Polariscope Systems. For observation and measurement of residual stress and birefringence" *Strainoptics Bulletin PS-1009*, Jan. 2009, pp. 1-4. http://www.strainoptics.com/files/PS-100%20Bulletin.pdf (Retrieved Aug. 20, 2014).

Anton, J., et al. "On the inhomogeneity of residual stresses in tempered glass panels" *Estonian Journal of Engineering* 18:1 (2011) 3-11.

PCT International Search Report mailed on Aug. 20, 2013 for PCT/EP2013/057469 filed on Apr. 10, 2013 in the name of Saint-Gobain Glass France.

* cited by examiner

METHOD AND ARRANGEMENT FOR MEASURING BLOWING STRUCTURES OF A PRESTRESSED DISC

CROSS REFERENCE TO RELATED APPLICATIONS

The present application is the US national stage of International Patent Application PCT/EP2013/057469 filed on Apr. 10, 2013 which, in turn, claims priority to European Patent Application EP 12165122.8 filed on Apr. 23, 2012.

The invention relates to a method for measuring blowing structures of a prestressed pane. The invention further relates to an arrangement for measuring blowing structures of a prestressed pane and its use.

Panes are frequently provided with prestressing. For this purpose, the panes are heated to a temperature above the lower annealing point and cooled quickly, by which means compressive stresses are formed on the surface of the pane and tensile stresses are formed in the core of the pane. Prestressed panes have increased thermal and mechanical strength compared to non-prestressed panes. If a prestressed pane breaks under a high load, fragments are formed from which, due to their shape and size, there is no risk of severe cutting injuries. Prestressed panes are used as single-pane safety glass, for example, as side windows or rear windows of motor vehicles.

For the rapid quenching of the panes during the prestressing process, the panes are typically impinged upon by a stream of air from a plurality of jets. Depending on the arrangement of the jets, an inhomogeneous distribution of stresses forms in the pane. The inhomogeneously distributed stresses result in a position-dependent interaction of the pane with light incident thereon. With suitable light and viewing conditions, structures can be detected on the pane that are frequently perceived by an observer as bothersome. Such visible structures as a result of the prestressing process are referred to, in the context of the invention, as blowing structures. They are also known, for example, as tempering marks, quench marks, or stress patterns. In the context of the invention, the expression "blowing structures" is understood to mean all optically perceivable structures which develop through treatment of pane during prestressing. The treatment need not necessarily include impingement with a stream of air.

In order to be able to objectively evaluate the extent of the blowing structures, a reproducible, quantitative measurement method is essential. A method for measuring blowing structures is known from WO 2011157815 A1. An essential fraction of the method described is the comparison of an optical measurement with the subjective evaluation of test panes by a group of individuals. The measurement method is, consequently, not completely objective. In addition, for the optical measurement, a movement of the test pane relative to the analysis unit is required, as a result of which the method described is complicated to execute.

From P. Castellini et al.: "Laser sheet scattered light method for industrial measurement of thickness residual stress distribution in flat tempered glass" (Optics and Lasers Engineering, vol. 50, no. 5, 2012, pp. 787-795), a method is known for measuring the stress profile along the thickness of the pane. With this method, it is required to couple laser radiation via the side edge into the pane to be examined. The method is, in particular, not applicable to prestressed panes in the automotive sector, since these panes are typically curved and have a ground side edge. With such panes, irradiation via the side edge is not possible.

The object of the present invention consists in making available an improved method for measuring blowing structures on a prestressed pane and an arrangement suitable therefor. The method should deliver an objective, quantitative measure for the extent of the blowing structures and be simple and reproducible to perform.

The object of the present invention is accomplished according to the invention by a method for measuring blowing structures of a prestressed pane, wherein at least
(a) at least one analysis area of the pane is irradiated with linearly polarized light from a radiation source at an angle of incidence $\theta_E$ and an image at least of the analysis area is recorded at an observation angle $\theta_A$ using at least one detector,
(b) the image is supplied to an evaluation unit, and
(c) by means of the evaluation unit
  (c1) a brightness profile is read along an analysis line in the image,
  (c2) the local maxima and the local minima of the brightness profile are determined, and
  (c3) an intensity index $I_{BS}$ is determined by means of the difference between a brightness mean $M_{max}$ of the local maxima and a brightness mean $M_{min}$ of the local minima.

The pane has a first surface and a second surface as well as the circumferential side edge. In the installation position, the intended examination through the pane occurs through the first and the second surface. The first surface is a surface of the pane that is turned toward the radiation source. The first surface of the pane is irradiated with the light of the radiation source. In the context of the invention, this means that the light, during passage through the pane, first strikes the first surface and, after that, strikes the second surface of the pane that is turned away from the light source. According to the invention, the analysis area of the pane is thus irradiated via the first surface of the pane with the light of the radiation source.

The term "prestressed pane" also includes, in the context of the invention, partially prestressed panes. A prestressed pane, in the narrower sense of the term, typically has surface compressive stresses from 85 MPa to 140 MPa and tensile stresses in the core from 40 MPa to 60 MPa. A partially prestressed pane typically has surface compressive stresses from 24 MPa to 52 MPa.

The object of the present invention is further accomplished according to the invention by an arrangement for measuring blowing structures of a prestressed pane, comprising at least:
  a radiation source, which irradiates at least one analysis area of the pane with linearly polarized light at an angle of incidence $\theta_E$,
  at least one detector, which records an image at least of the analysis area at an observation angle $\theta_A$, and
  an evaluation unit, which receives the image, reads a brightness profile along an analysis line in the image, determines the local maxima and the local minima of the brightness profile, and determines an intensity index $I_{BS}$ by means of the difference between a brightness mean $M_{max}$ of the local maxima and a brightness mean $M_{min}$ of the local minima.

Parallel polarized radiation fractions are reflected on passage through a pane to a small extent on the surfaces of the pane as perpendicular polarized radiation fractions. The inhomogeneous stress distribution in the pane created in the prestressing process results in a position-dependent interaction of the light with the pane (Paul Chagnon: "Optics for People Stuck in Traffic: Stress Patterns", The Physics Teacher 32 (1994), p. 166f.). In particular, a position-dependent rotation of the polarization direction of the light occurs on passage through the pane. In areas in which no rotation of the polarization plane occurs, the light is reflected on the second surface of the pane (exit surface) to the same extent as on the first surface (entry surface). In areas in which a rotation of the polarization plane occurs, the ratio of the parallel polarized radiation fractions to the perpendicular polarized radiation fractions is changed and the level of reflection on the second surface of the pane differs from the level of reflection on the first surface. The total light reflected from the pane as well as the total light transmitted through the pane thus has a position-dependent intensity that mirrors the inhomogeneous distribution of the stresses in the pane. The position-dependent intensity of the reflected and transmitted light results in an optically perceivable pattern of brighter and darker areas. The more unevenly the stresses are distributed in the pane, the more pronounced the blowing structures and the greater the difference in brightness between the brighter and darker areas. The position-dependent intensity of the reflected and/or transmitted light is captured by the detector in the form of an image, and subsequently analyzed quantitatively. The method for measuring blowing structures according to the invention delivers an objective, reproducible quantitative measure of the extent of the blowing structures that are caused by the inhomogeneous distribution of the stresses. Since at least the entire analysis area is irradiated by the radiation source and detected by the detector, no movement of the pane is necessary, as result of which the method is simple to perform. These are major advantages of the invention.

The irradiation of the analysis area via the pane surface according to the invention has critical advantages compared to the irradiation via the side edges. The method according to the invention is applicable to a far greater variety of panes. The method is, in particular, also applicable to panes in the automotive sector, which are typically curved and have a ground side edge, in particular, a dull ground side edge. With such panes, irradiation of the analysis area via the side edge is not possible.

In the view of the inventor, the areas in which no rotation of the polarization plane of the light occurs are stress-free areas or areas with quantitatively identical major stresses. The areas in which a rotation of the polarization plane occurs are areas with quantitatively different major stresses, with the extent of the rotation of the polarization plane dependent on the difference in the major stresses.

The analysis area is, in the context of the invention, an area of the pane for which the brightness profile is to be determined in the method according to the invention. The analysis area is the smallest possible area that has to be irradiated by the light of the radiation source and of which an image must be recorded by the detector in order to be able to perform a desired analysis of the blowing structures. The analysis area has a first surface that is an area of the first surface of the pane. The analysis area has a second surface that is an area of the second surface of the pane. The thickness of the analysis area corresponds to the thickness of the pane. The analysis area according to the invention is preferably arranged in the center of the pane. The first surface of the analysis area is then arranged in the center of the first surface of the pane, and the second surface of the analysis area is arranged in the center of the second surface of the pane. This means that the geometric center of the first surface of the analysis area corresponds roughly to the geometric center of the first surface of the pane and that the geometric center of the second surface of the analysis area corresponds roughly to the geometric center of the second surface of the pane. The size of the analysis area is suitably selected such that it includes a sufficient number of blowing structures, i.e., a sufficient number of areas with different levels of reflection ("bright" and "dark" areas). The analysis area has, for example, a length and width of 30 cm. The analysis area can, however, also be selected significantly larger. The analysis area can, in principle, even include the entire pane.

The radiation source irradiates, according to the invention, at least the analysis area of the pane. The radiation source can, of course, irradiate a larger area of the pane that contains the analysis area. The radiation source can, for example, irradiate the entire pane.

The detector records, according to the invention, an image at least of the analysis area of the pane. The detector can, of course, also record an image of a larger area of the pane that contains the analysis area.

The light of the radiation source is linearly polarized. With linear polarization, the direction of oscillation of the electrical field is constant. The magnitude and sign of the electrical field change periodically. The specified direction of oscillation is referred to as the polarization direction.

The light of the radiation source is preferably parallel polarized (p-polarized) or predominantly p-polarized relative to the first surface of the pane. P-polarized means that the polarization direction the radiation strikes the pane is in the plane of incidence. The plane of incidence is formed by the incidence vector and the surface normal of the pane at the point where the radiation strikes the pane. The particular advantage of p-polarized light resides in its low reflection compared to perpendicular polarized (s-polarized) light. The p-polarized light is reflected on the first surface to a lesser extent. In areas of the pane, in which a rotation of the polarization direction occurs, the perpendicular polarized radiation fraction, which is more intensely reflected on the second surface, is increased. The intensity of all the light reflected by the pane is thus increased in these areas. P-polarized light thus results in a low basic reflection, while areas in which a rotation of the polarization direction occurs are discernible in the reflection as bright areas. It has been demonstrated that the blowing structures are particularly readily discernible under these conditions.

Due to the usual inaccuracies in the practical performance, the polarization direction can, of course, easily deviate to the usual extent from the ideal p-polarization, for example, by an amount from 0° to 10°.

However, the method according to the invention can also be performed with s-polarized light or with light that contains p-polarized and s-polarized radiation fractions. The position-dependent rotation of the polarization direction also results in these cases in a position-dependent level of reflection and thus in a brightness pattern of all the light reflected and/or transmitted by the pane, which can be used for an analysis of the blowing structures according to the invention.

The pane, whose blowing structures are to be measured, can be flat, as is, in particular, in the architectural sector, for example, in the access or window area. Alternatively, the pane can be curved slightly or greatly in one or a plurality of spatial directions. Such curved panes appear, in particular for glazings in the automotive sector. Typical radii of curvature of the curved panes are within the range from roughly 10 cm to roughly 40 m. The radius of curvature need not be constant over the entire pane; greatly and less greatly curved areas can be present in one pane.

The pane is preferably curved. The method according to the invention can advantageously be used on such curved panes.

The pane preferably has a ground, in particular a dull ground side edge. The entire surface of the side edge is preferably dull ground. The method according to the invention can advantageously be used on such panes.

In an advantageous embodiment of the invention, the pane is a motor vehicle window pane. The motor vehicle window pane is preferably curved and has a dull ground edge.

In the case of a curved pane, the direction of the surface normal is position-dependent within the surface of the analysis area. Thus, the orientation of the plane of incidence can also be position-dependent. The geometric center of the first surface of the analysis area is logically used to set the desired polarization direction of the light. The radiation is deemed p-polarized according to the invention when the polarization direction lies in the plane that is spanned by the incidence vector and the surface normal in the center of the first surface of the analysis area.

The first surface of the pane turned toward the radiation source can be turned toward the detector and/or turned away from the detector. If the first surface is turned toward the detector, all the radiation reflected from the pane is detected by the detector. The detector records an image at least of the first surface of the analysis area. If the first surface is turned away from the detector and if the second surface is thus turned toward the detector, the radiation transmitted through the pane is detected by the detector. In this case, the detector records an image at least of the second surface of the analysis area. In both cases, the extent of the blowing structures can be analyzed in the image. Also, an image from a first detector and a second detector can be recorded in each case, with the first surface of the pane turned toward the first detector and turned away from the second detector.

In a particularly advantageous embodiment, the first surface of the pane turned toward the radiation source is turned toward the detector. The detector detects the radiation reflected from the pane. Such a reflection measurement has, compared to a transmission measurement, the advantage that it can be used on printed panes. Such printed panes, in particular panes provided with silkscreen printing, are, in particular, common in the automotive sector.

The level of reflection of the linear polarized radiation depends on the angle of incidence of the radiation on the surface of the pane. The level of reflection is the ratio of reflected radiation intensity to incident radiation intensity. The angle of incidence is the angle between the incidence vector and the surface normal of the pane at the point where the radiation strikes the surface of the pane. The difference between the level of reflection of parallel polarized radiation and the level of reflection of perpendicular polarized radiation is particularly large when the angle of incidence $\theta_E$ is the same as the so-called Brewster angle. With incidence of light below the Brewster angle, the level of reflection for p-polarized radiation is ideally equal to zero. The Brewster angle on an air-glass transition according to the invention is roughly 57° (with the index of refraction of air $n_{Air}=1$ and the index of refraction of glass $n_{Glass}=1.55$).

In the case of a curved pane, the direction of the surface normal within the analysis area of the pane is position-dependent. Thus, the angle of incidence $\theta_E$ is also position-dependent. The geometric center of the first surface of the analysis area is logically used to set the desired angle of incidence $\theta_E$. The angle of incidence $\theta_E$ according to the invention is preferably measured in the center of the first surface of the analysis area.

The angle of incidence $\theta_E$ is preferably from 20° to 70°, particularly preferably from 40° to 65°, quite particularly preferably from 55° to 60°, especially roughly 57°. In this range, the difference between the level of reflection of p-polarized light and the level of reflection of s-polarized light is particularly large and the brightness pattern caused by the blowing structures advantageously appears particularly clearly.

The ranges indicated for the angle of incidence $\theta_E$ are particularly advantageous when the light reflected by the pane is detected by the detector. When the light transmitted through the pane is detected by the detector, the angle of incidence $\theta_E$ can also be, for example, from 0° to 20°, preferably from 0° to 10°, especially roughly 0°.

The radiation source is preferably a flat (two-dimensional) radiation source. This is understood to mean a radiation source that emits light via an emission surface area and that can be perceived not as a point radiation source relative to the dimensions of the pane. Such a virtual point radiation source is, for example, a laser or a lightbulb. The emission surface area of the flat radiation source can, for example, have a size of at least 0.5 m² or at least 1 m². The emission surface area of the flat radiation source can, in principle, be curved, but is, however, flat in a particularly preferred embodiment. Then, the propagation direction of the light is constant over the emission surface area. Thus, the entire analysis area of the pane surface can advantageously be irradiated with radiation of the same propagation direction. The radiation source comprises quite particularly preferably at least a so-called polarization wall. A polarization wall comprises at least one, typically a plurality of, primary radiation sources, for example, a plurality of fluorescent tubes arranged parallel to each other, behind a strongly scattering glass pane, typically an opal glass pane. Upon passage through the scattering glass pane, flat, unpolarized radiation is generated from the radiation of the primary radiation source. Linearly polarized radiation is generated by a flat polarization filter on the side of the scattering glass pane turned away from the primary radiation sources.

The radiation source preferably emits radiation in the visible spectral range. This is, on the one hand, advantageous due to the simple availability of suitable radiation sources and detectors. On the other, a bothersome effect of the blowing structures for a viewer observer occurs in conjunction with visible light such that the use of visible light for the quantitative measurement of blowing structures is reasonable. However, the light of the radiation source need not cover the entire visible spectral range. Also, the radiation of the radiation source need not be restricted to the visible spectral range. The radiation of the radiation source can contain radiation fractions from other spectral ranges, for example, IR radiation and/or UV radiation.

The detector preferably comprises a camera with a two-dimensional image sensor, for example, a CCD sensor or an active pixel sensor (APS sensor, CMOS sensor). Due to the better availability and the lower costs, a camera with a CCD sensor is preferred. An image at least of the entire analysis area can be advantageously recorded by the two-dimensional image sensor. The image is, of course, recorded while the pane is irradiated with light by the radiation source.

The detector can include further optical elements, for example, optical filters such as gray filters or color filters.

The detector is preferably arranged such that the radiation reflected on the pane or transmitted through the pane is optimally detected. The detector is aimed at an ideal location on the surface of the pane that is turned toward the detector. If the detector is a camera, the objective is preferably focused on the ideal location. The angle of observation $\theta_A$ is then the angle between the connecting line between the detector and the ideal location, on the one hand, and the surface normals of the pane at the ideal location, on the other. Reasonably selected as the ideal location on the surface of the pane is the geometric center of the surface of the analysis area that is turned toward the detector. The angle of observation $\theta_A$ is preferably from 20° to 70°, particularly preferably from 40° to 65°, quite particularly preferably from 55° to 60°, in particular roughly 57°. The angle of observation $\theta_A$ is preferably quantitatively equal to the angle of incidence $\theta_E$ or deviates only to a small extent from the angle of incidence $\theta_E$, for example, by an amount from 0° to 10°. If the first surface of the pane is turned toward the radiation source and the detector, the radiation source and the detector are preferably arranged opposite one another relative to the surface normal in the geometric center of the first surface of the analysis area. Then, the reflected light can be detected particularly advantageously.

The first surface of the pane turned toward the radiation source is preferably the outer surface of the pane. Here, the term "outer surface" designates the surface of the pane that is provided to be turned toward the external surroundings of a space that the pane delimits in the installation position of the pane. If the pane is, for example, a motor vehicle window pane, the outer surface is, in the installation position, turned toward the external surroundings and turned away from the interior of the motor vehicle.

The image is preferably recorded in front of a black or dark background. Then, the blowing structures are particularly advantageous to discern. Particularly preferably, the method according to the invention is performed in a darkened room, with the radiation source the unique source of light.

The evaluation unit preferably comprises at least a computer with image analysis software that is suitable for reading the brightness value of each image point (pixel) of the image recorded by the detector.

According to the invention, the image recorded by the detector is supplied to the evaluation unit. This can occur via a direct connection between the detector and the evaluation unit, for example, via a cable or a wireless connection. The transmission of the image can occur automatically or be prompted by a command of the user. However, the image can also be supplied to the evaluation unit by other suitable means, for example, via a server or a storage medium.

The blowing structures are discernible in the image recorded by the detector as a pattern of darker and brighter areas. During prestressing, the pane is typically impinged upon by a stream of air from a plurality of parallel rows of jets. The pattern of darker and brighter areas is caused by the arrangement of the jets. Consequently, the brighter areas in the image are arranged along lines parallel to each other. The brightness profile along an analysis line is read according to the invention by the evaluation unit.

The analysis line is preferably selected such that it runs through a group of bright areas that are arranged on the same one of the lines running parallel to each other. The analysis line preferably runs centrally through the bright areas.

The image recorded by the detector can be processed in the usual manner before the analysis of the brightness profile. The data volume and/or the image dimensions can, for example, be reduced electronically.

The brightness profile is, in the context of the invention, a plotting of the brightness value determined against the position along the analysis line, which can, for example, be expressed by an arbitrary length scale (for example, a numbering of the successive pixels). The brightness profile along the analysis line presents a wavelike profile with a sequence of local maxima (center of the bright areas in the image) and local minima (center of the dark areas in the image). In the method according to the invention, the position of the local maxima and minima is identified and the respective brightness value is read. The identification of the local maxima and minima preferably occurs automatically using a suitable algorithm, but can be done manually. The data of the brightness profile can be smoothed by a suitable algorithm before the analysis of the local maxima and minima.

The analysis area is preferably selected such that the brightness profile contains at least 3 local maxima. The analysis area is, in particular, preferably selected such that the brightness profile contains from 5 to 20, quite particularly preferably from 8 to 15 local maxima. This is particularly advantageous with regard to a reliable and reproducible measurement of the blowing structures, on the one hand, and a time-saving evaluation of the measurement, on the other.

A first mean, which is referred to in the context of the invention as brightness mean $M_{max}$ of the local maxima, is formed from the brightness values of the local maxima of the brightness profile. A second mean, which is referred to in the context of the invention as brightness mean $M_{min}$ of the local minima, is formed from the brightness values of the local minima of the brightness profile. The brightness means $M_{max}$ and $M_{min}$ are preferably arithmetic means. However, in principle, other means can also be used if they are deemed reasonable by the person skilled in the art, for example, the geometric mean, the harmonic mean, or the quadratic mean.

The quantitative difference between the brightness mean $M_{max}$ of the local maxima and the brightness mean $M_{min}$ of the local minima is referred to, in the context of the invention, as the intensity index $I_{BS}$ of the blowing structures. The intensity index $I_{BS}$ is a quantitative and objective measure of the extent of the blowing structures. Large values of the intensity index $I_{BS}$ point to a large difference in the level of reflection in the bright areas compared to the dark areas and, thus, to pronounced blowing structures. Small values of the intensity index $I_{BS}$ point to a small difference in the level of reflection in the bright areas compared to the dark areas and, thus, to less pronounced blowing structures. Using the intensity index $I_{BS}$, different panes can be quantitatively compared to one another with regard to the extent of the blowing structures. Due to the objectivity and reproducibility of the method according to the invention, the measurements to be compared on different panes can even be taken at different times.

In an advantageous embodiment of the arrangement according to the invention for measuring blowing structures, the preferably flat radiation source is arranged vertically. This means that the area via which the emission of the light occurs is arranged vertically, i.e., an angle of roughly 90° relative to the horizontal. It has been demonstrated that the blowing structures can be observed particularly well when the pane is arranged at an angle relative to the horizontal that differs by at most 15°, preferably at most 5° from the angle of the polarization direction of the light of the radiation source relative to the horizontal. Particularly preferably, the angle relative to the horizontal at which the pane is arranged corresponds to the angle of the polarization direction of the light of the radiation source relative to the horizontal. The angle relative to the horizontal at which the pane is arranged and the angle of the polarization direction of the light of the radiation source relative to the horizontal are dimensioned in a value range from 0° to 90°. If a polarization wall as a radiation source, for example, has a polarization direction that is arranged at an angle of roughly 40° relative to the horizontal, the blowing structures can be observed particularly well when the pane is arranged at an angle from 30° to 60°, preferably from 40° to 50°, and in particular roughly 45° relative to the horizontal. In the case of curved panes, the tangential plane in the center of the analysis area can, for example, be used to assess the angle relative to the horizontal. For this, the pane can be arranged in a suitable mounting that permits a reliable and reproducible positioning of the pane.

The detector can, for example, be positioned on a tripod or another suitable mounting. The relative arrangement of the pane and the detector can, for example, be accomplished using floor markings. The mounting of the detector and the mounting of the pane can, alternatively, be permanently connected to one another, for example, on a common frame. Thus, advantageously, a quick and easy to produce, reproducible relative arrangement of the pane and the detector is achieved.

The reproducible relative orientation of the radiation source and the pane can, for example, be accomplished using floor markings. The radiation source and the mounting of the pane and/or of the detector can also be stably connected to each other.

The pane preferably contains glass, particularly preferably flat glass, float glass, quartz glass, borosilicate glass, and/or soda lime glass. The thickness of the pane can vary widely and thus be excellently adapted to the requirements of the individual case. The thickness of the pane is preferably from 1.0 mm to 25 mm and particularly preferably from 1.4 mm to 5 mm. The size of the pane can vary widely and is determined by its intended use. The pane has, for example, in the automotive and the architectural sector, customary areas from 200 $cm^2$ all the way to 20 $m^2$.

The pane can be largely transparent and, for example, can have a total transmission of more than 70%. However, the pane can also be stained and/or tinted and, for example, can have a total transmission of less than 50%. The term "total transmission" is based on the method for testing light transmission of a motor vehicle windows specified by ECE-R 43, Annex 3, §9.1.

The invention further includes the use of the arrangement according to the invention for quantitative measurement of blowing structures on prestressed panes, in particular for quantitative comparative measurement of different panes. The panes are preferably panes in buildings, in particular in access or window areas, in furniture and devices, in particular electronic devices with a cooling or heating function, or in means of transportation for travel on land, in the air, or on water, in particular in trains, ships, and motor vehicles, for example, side windows, roof panels, and/or rear windows as single-pane safety glass.

The invention is explained in detail in the following with reference to drawings and exemplary embodiments. The drawings are schematic representations and not true to scale. The drawings in no way restrict the invention.

Figure 2A:
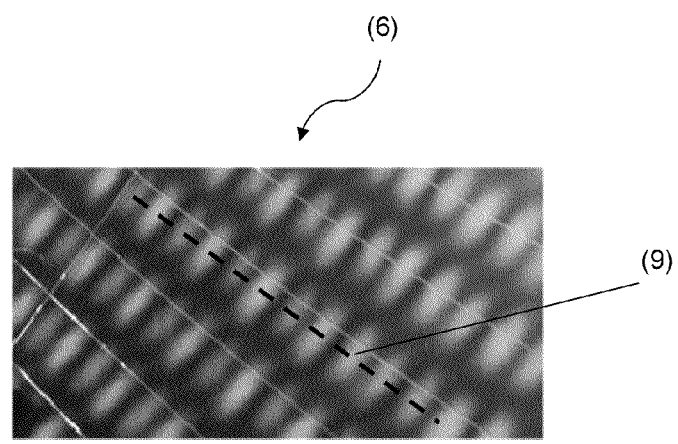
Figure 2B:
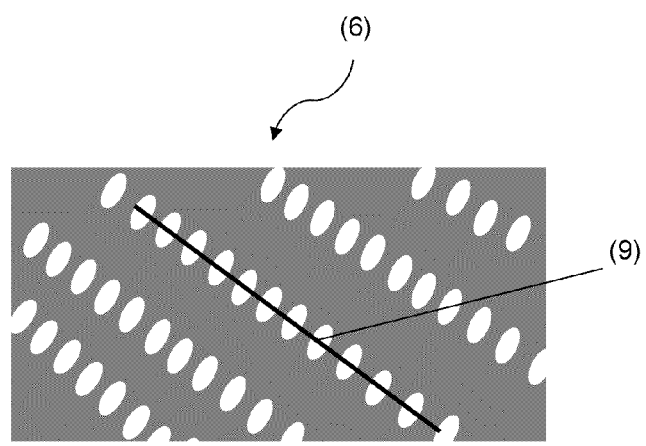
Figure 3:
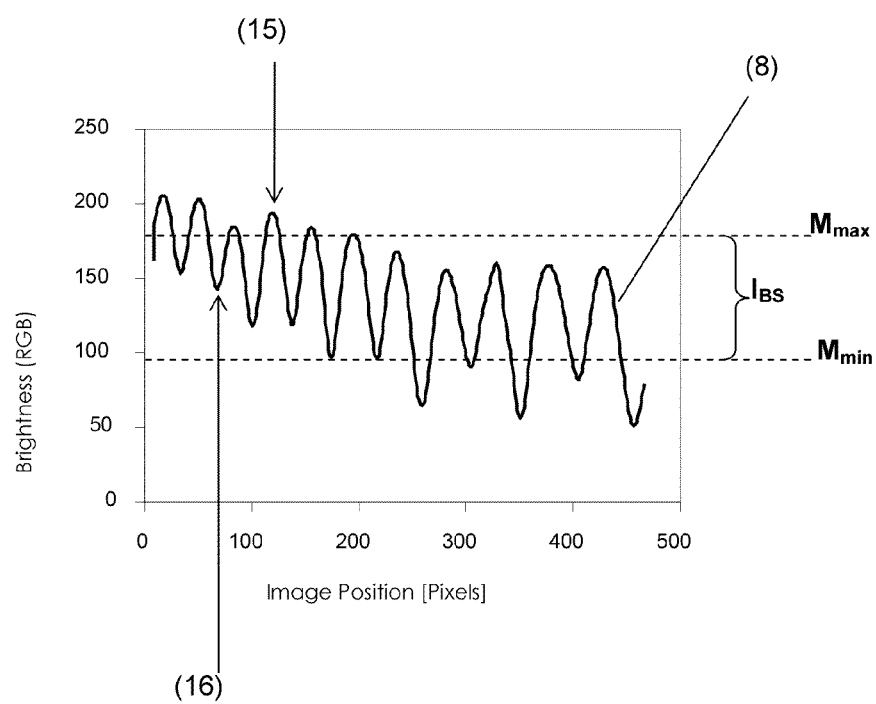
Figure 4A:
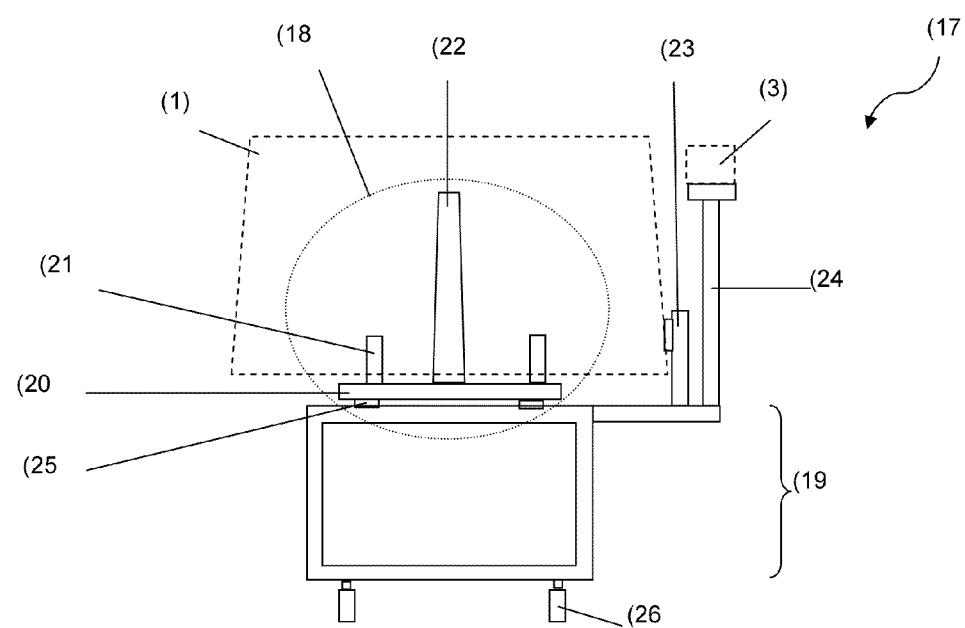
Figure 4B:
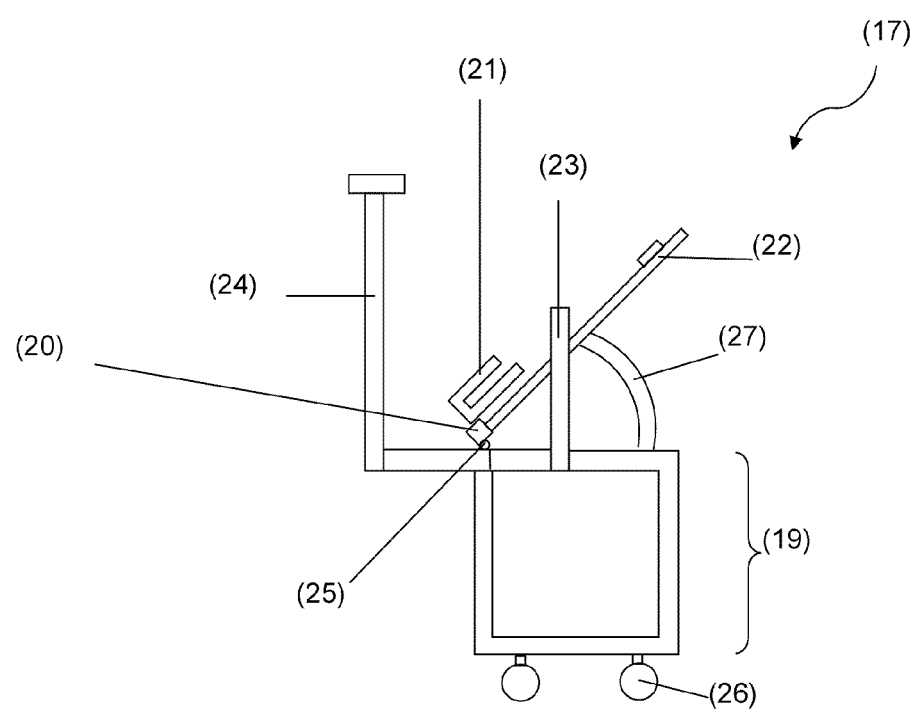
Figure 5:
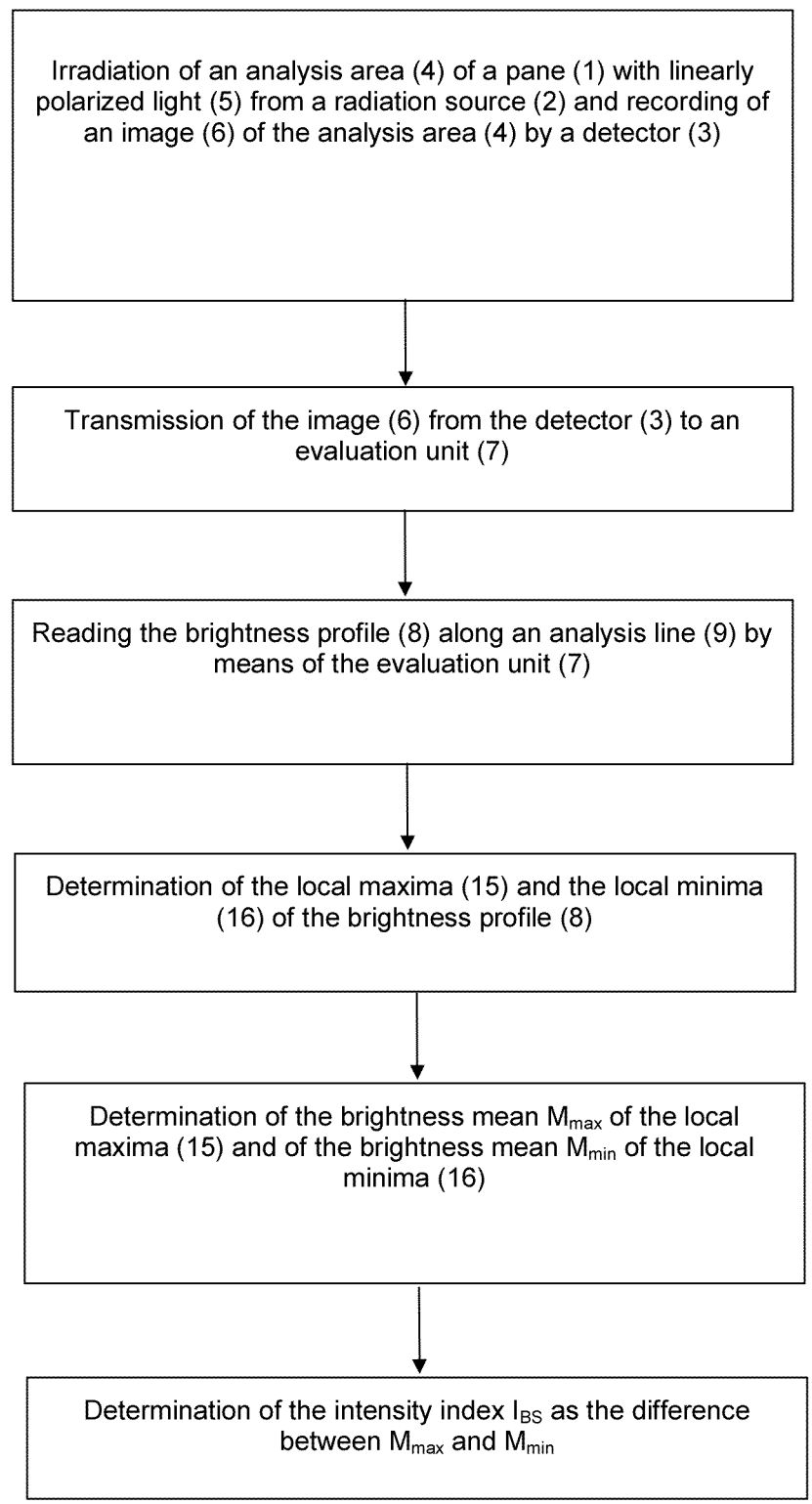

They depict:

FIG. 1 a schematic representation of the arrangement according to the invention for measuring blowing structures on a prestressed pane, FIG. 2a an image recorded by the detector, FIG. 2b a schematic representation of the image from FIG. 2a, FIG. 3 a diagram of the brightness profile along the analysis line in FIG. 2a, FIG. 4a a front elevation of a mounting arrangement for the pane and the detector, FIG. 4b a side view of the mounting arrangement from FIG. 4a, and FIG. 5 a detailed flow chart of one embodiment of the method according to the invention for measuring blowing structures of a prestressed pane.

FIG. 1 depicts a schematic representation of the arrangement according to the invention for measuring blowing structures of a prestressed pane 1. The pane 1 is a rear window pane of an automobile. The pane 1 has the curvature and edge grinding customary for rear window panes. The pane 1 is a 3-mm-thick single-pane safety glass made of soda lime glass with a width of 150 cm and a height of 80 cm. The pane 1 is thermally prestressed and has, for example, a surface compressive stress of roughly 120 MPa and a tensile stress in the core of roughly 60 MPa. As a result of the prestressing process, the pane 1 has inhomogeneously distributed stresses, which result in so-called blowing structures that are visually perceptible under certain observation and light conditions as patterns of brighter and darker areas. By means of the method according to the invention, the extent of the blowing structures can be determined quantitatively. Thus, for example, panes prestressed using different methods can be compared with each other with regard to the extent of the blowing structures.

The arrangement according to the invention comprises a radiation source 2. The pane 1 is curved, as is customary for rear window panes. The convex first surface (I) of the pane 1, which is provided, in the installation position of pane 1 as the outer surface, is turned toward the radiation source 2 such that the light 5 of the radiation source 2 during passage through the pane 1 first strikes the first surface (I). The radiation source 2 is a polarization wall. The polarization wall comprises a plurality of fluorescent tubes arranged parallel to each other behind an opal glass pane and a flat polarization filter on the side of the opal glass pane turned away from the florescent tubes. Linearly polarized white light 5 in the visible spectral range is emitted by the radiation source 2 via an emission surface with a height of 150 cm and a width of 200 cm. The entire surface (I) of the pane 1, minus any shadowed areas, is irradiated by the flat radiation source 2. In particular, an analysis area 4 is completely irradiated. The analysis area 4 is provided for the evaluation of the measurement of blowing structures. The analysis area 4 has, for example, a length and width of 30 cm and is arranged roughly in the geometric center of the pane 1. The analysis area 4 has a first surface, which is an area of the first surface (I) of the pane 1, with the first surface of the analysis area 4 arranged in the geometric center of the first surface (I) of the pane. The analysis area 4 has a second surface, which is an area of the second surface (II) of the pane 1, with the second surface of the analysis area 4 arranged in the geometric center of the second surface (I) of the pane.

The light 5 of the radiation source is parallel polarized relative to the surface (I). The direction of oscillation of the electromagnetic waves described by the polarization vector 12 lies in the plane of incidence 11, which is formed by the incidence vector of light 5 and the surface normal 10 of the surface (I). Parallel polarized light is less highly reflected on the surfaces of the pane 1 than perpendicular polarized light. This effect is particularly pronounced when the angle of incidence $\theta_E$ corresponds roughly to the Brewster angle. The Brewster angle for an air-gas transition is roughly 57° and the angle of incidence $\theta_E$ is selected accordingly.

Since the pane 1 is curved, the direction of the surface normal 10 within the analysis area 4 is positioned-dependent. To set and assess the polarization direction and the angle of incidence $\theta_E$, the surface normal 10 in the geometric center of the first surface of the analysis area 4 is used.

The light 13 reflected from the pane 1 has a position-dependent intensity. Inhomogeneously distributed stresses in the pane 1 produced by the prestressing process are the reason for this. The stresses result in a position-dependent rotation of the polarization vector 12 at the time of passage through the pane 1. If the polarization vector 12 is not rotated, the light 5 strikes the surface (II) of the pane 1, which is turned away from the radiation source 2, parallel polarized. The light 5 is, in this case, reflected on both surfaces (I) and (II) only to a small extent and the intensity of all the light 13 reflected by the pane 1 is low. If the polarization vector 12 is rotated, the light 5 strikes the surface (II) with an increased perpendicular polarized radiation fraction, which is reflected significantly stronger than parallel polarized light. The intensity of all the light 13 reflected by the pane 1 is thus increased, with the level of reflection dependent on the extent of the rotation of the polarization vector 12. As a result of the inhomogeneously distributed stresses in the pane 1, the reflected light 13 thus forms a pattern of darker and brighter areas.

The arrangement according to the invention further comprises a detector 3. The surface (I) of the pane 1 turned toward the radiation source 2 is also turned toward the detector 3. The detector 3 is a camera with a CCD sensor. The pattern of the position-dependent intensity of the reflected light 13 is detected by the detector 3. For this purpose, a photograph is taken, which shows at least the analysis area 4, but typically a larger area of the pane 1. For this, the camera is aimed and focused on the center of the first surface of the analysis area 4. The angle of observation $\theta_A$ is, for example, roughly 60° and is thus selected near the Brewster angle. Thus, the pattern of the position-dependent intensity of the reflected light 13 can be detected particularly well.

The arrangement according to the invention further comprises an evaluation unit 7. The evaluation unit 7 is, for example, connected to the detector 3 via a connection cable 14. The photograph is transmitted via the connection cable 14 from the detector 3 to the evaluation unit 7. The evaluation unit 7 is a computer with suitable image analysis software that can read out the brightness value of each pixel of the photograph.

FIG. 2a depicts a detail (707×480 pixels) of an image 6, which shows the analysis area 4, more precisely, the first surface of the analysis area 4. The image 6 is a photograph and was taken by the camera as detector 3 in the arrangement according to FIG. 1. The camera as detector 3 was, in that case, a digital single-lens reflex camera of the type Canon EOS 30D with an objective of the type Canon EF-S 18-55 mm. The image 6 was taken with manual focusing on the center of the image and selection of the following parameters: focal distance 55 mm, ISO 400, aperture 22, color space sRGB, exposure time 0.8 s. In the image 6, the blowing structures are clearly discernible as patterns of bright areas in front of a dark background. The bright areas are arranged along lines parallel to each other. The pattern results from the arrangement of jets with which the pane 1 was impinged upon by a stream of air during prestressing. The figure further depicts an analysis line 9. The analysis line 9 runs along one of the lines arranged parallel to each other, along which the bright areas are arranged. The analysis line 9 is selected such that it runs roughly centrally through the bright regions. The brightness profile of the image 6 along the analysis line 9 is used for quantification of the blowing structures.

FIG. 2b is a schematic depiction of the image 6 of FIG. 2a. The bright areas in front of the dark background and the analysis line 9 are discernible.

FIG. 3 depicts a diagram of the brightness profile 8 along the analysis line 9 in the image 6 of FIG. 2a. The analysis area 4 and the analysis line 9 are selected such that eleven of the bright areas are covered. The creation and analysis of the brightness profile 8 occurs in the evaluation unit 7. The brightness profile 8 was generated using image analysis software, which reads the brightness value (RGB color space, 256 brightness levels) of each pixel along the analysis line 9. The brightness profile 8 depicts a wavelike profile with eleven maxima 15 and eleven local minima 16. The arithmetic mean is formed from the brightness values of the local maxima 15 and thus the brightness mean $M_{max}$ of the local maxima 15 is determined. The arithmetic mean is formed from the brightness values of the local minima 16 and the brightness mean $M_{min}$ of the local minima 16 is determined. The brightness mean $M_{max}$ in the example depicted is 177, the brightness mean $M_{min}$ is 96. The quantitative difference between the brightness mean $M_{max}$ and the brightness mean $M_{min}$ is, in the context of the invention, referred to as the intensity index $I_{BS}$. The intensity index $I_{BS}$ is a quantitative measure of the extent of the blowing structures. The intensity index $I_{BS}$ is 81 in the example depicted. The lower the value of the intensity index $I_{BS}$, the lower the mean brightness difference between the bright area and the dark areas in image 6 and the more uniform the overall reflection of the pane appears. Using the intensity index $I_{BS}$, comparative panes can be compared to each other with regard to the visibility of the blowing structures.

The brightness profile 8 has, in the example depicted, a decreasing trend. The reason for this is the bending of the pane 1, which results in a position-dependent direction of the surface normals 10 within the analysis area 4. Thus, the reflection behavior of the light 5 is likewise position-dependent. Nevertheless, the brightness means $M_{max}$ and $M_{min}$ deliver a meaningful intensity index $I_{BS}$, by means of which comparative panes can be compared to each other, in particular, if the comparative panes have the same or similar bending. For example, panes of the same type that were prestressed in a different manner can be compared to one another.

Under identical conditions, 50 measurements were performed on a reference pane 1. The measurements delivered a mean for the intensity index $I_{BS}$ of 84 with an empirical variance of 0.5. The intensity index $I_{BS}$ is thus a highly reproducible measure for blowing structures.

The fact that an objective quantitative and reproducible measure of the extent of blowing structures can be determined using the method according to the invention and the arrangement according to the invention for measuring blowing structures of a prestressed pane was unexpected and surprising for the person skilled in the art.

FIG. 4a and FIG. 4b depict in each case a detail of a suitable mounting arrangement 17 for the pane 1 and the detector 3. The mounting arrangement 17 comprises a pane mount 18, a detector mount 24, and a positioning stop 23, which are arranged on a common frame 19. By means of the mounting arrangement 17, a stable and reproducible arrangement of the pane 1 and the detector 3 is achieved. Thus, with a comparative measurement, a constant angle of observation $\theta_A$ is ensured. The frame 19 is mounted on rollers 26, with which the mounting arrangement 17 can be moved simply, for example, for alignment relative to the light source 2. The positioning stop 23 enables a reproducible arrangement of the pane 1 on the pane mount 18 when different panes 1 of the same type are to be examined in a comparative measurement. Thus, the comparability of the measurement results is ensured. The pane mount 18 comprises a horizontal base element 20, on which a support element 22 and two support brackets 21 are arranged. The bottom edge of the pane 1 is introduced into the support brackets 21 and the pane 1 is leaned against the support element 22. The arrangement of the pane 1 is durably stable and reproducible. The base element 20 is connected to the frame 19 by two hinges 25. Thus, the pane mount 18 can be tipped and the angle between the pane 1 and the horizontal can be set. The desired angle is thus durably set by means of an angle fixing mechanism 27 arranged on the side of the support element 22 turned away from the pane 1. The angle fixing mechanism 27 is, for example, a metal rail in the form of a circular arc segment, of which the center of the circle is arranged on the connecting line between the hinges 25. The metal rail has a recess that runs parallel to the circular arc segment shaped edges and through which a screw connected to the frame 19 is guided. When the screw is loosened, the pane mount 18 can be tipped, with the screw sliding in the recess of the angle fixing mechanism 27. In the desired position of the pane mount 18, the screw is tightened and the pane mount 18 is thus durably and stably fixed.

FIG. 5 depicts a flowchart of an exemplary embodiment of the method according to the invention for measuring blowing structures on a prestressed pane 1.

LIST OF REFERENCE CHARACTERS (1) pane
(2) radiation source
(3) detector
(4) analysis area of the pane 1
(5) light from the radiation source 2
(6) image
(7) evaluation unit
(8) brightness profile of the image 6 along the analysis line 9
(9) analysis line in the image 6
(10) surface normal
(11) planes of incidence
(12) polarization vector of the light 5
(13) light reflected by the pane 1
(14) connection cable
(15) local maximum of the brightness profile 8
(16) local minimum of the brightness profile 8
(17) mounting arrangement
(18) pane mount of the mounting arrangement 17
(19) frame of the mounting arrangement 17
(20) base element of the pane mount 18
(21) support bracket of the pane mount 18
(22) support element of the pane mount 18
(23) positioning stop of the mounting arrangement 17
(24) detector mount of the mounting arrangement 17
(25) hinge of the pane mount 18
(26) roller of the mounting arrangement 17
(27) angle fixing mechanism of the pane mount 18
(I) first surface of the pane 1
(II) second surface of the pane 1
$\theta_E$ angle of incidence
$\theta_A$ angle of observation
$M_{max}$ brightness mean of the local maxima 15
$M_{min}$ brightness mean of the local minima 16
$I_{BS}$ intensity index

The invention claimed is:

1. A method for measuring blowing structures of a prestressed pane, comprising:
   (a) irradiating at least one analysis area of the pane with linearly polarized light from a radiation source at an angle of incidence, wherein a first surface of the pane is turned toward the radiation source, and an image at least of the analysis area is recorded at an angle of observation using at least one detector,
   (b) supplying the image to an evaluation unit, and
   (c) by means of the evaluation unit
      (c1) reading a brightness profile along an analysis line in the image,
      (c2) determining local maxima and local minima of the brightness profile, and
      (c3) determining an intensity index by means of a difference between a brightness mean of the local maxima and a brightness mean of the local minima.

2. The method according to claim 1, wherein the surface of the pane turned toward the radiation source is turned toward the detector.

3. The method according to claim 1, wherein the light is parallel polarized.

4. The method according to claim 1, wherein the radiation source is a two-dimensional radiation source and preferably comprises at least one polarization wall.

5. The method according to claim 1, wherein the angle of incidence and/or the angle of observation is from 20° to 70°, preferably from 40° to 65°, particularly preferably from 55° to 60°.

6. The method according to claim 1, wherein the detector comprises at least one camera with a two-dimensional image sensor, preferably a CCD sensor.

7. The method according to claim 1, wherein the surface of the pane turned toward the radiation source is the outer surface of the pane.

8. The method according to claim 1, wherein the pane contains glass, preferably flat glass, float glass, quartz glass, borosilicate glass, and/or soda lime glass and preferably has a thickness from 1.0 mm to 25 mm, particularly preferably from 1.4 mm to 5 mm.

9. The method according to claim 1, wherein the brightness profile contains at least 3, preferably from 5 to 20, particularly preferably from 8 to 15 local maxima.

10. The method according to claim 1, wherein the method is carried out in a room with the radiation source as the only light source.

11. The method according to claim 1, wherein the evaluation unit comprises at least a computer with image analysis software.

12. The method according to claim 1, wherein the angle of incidence and the polarization direction of the light are measured in the geometric center of the surface of the analysis area turned toward the radiation source.

13. An arrangement for measuring blowing structures of a prestressed pane, comprising at least:
   a radiation source, which irradiates at least one analysis area of the pane with linearly polarized light at an angle of incidence, wherein a first surface of the pane is turned toward the radiation source,
   at least one detector, which records an image at least of the analysis area at an angle of observation, and
   an evaluation unit, which receives the image, reads a brightness profile along an analysis line in the image, determines local maxima and local minima of the brightness profile, and determines an intensity index by means of a difference between a brightness mean of the local maxima and a brightness mean of the local minima.

14. The arrangement according to claim 13, further comprising a mounting arrangement, which contains a pane mount and a detector mount, preferably on a common frame.

15. A method comprising:
   using the arrangement according to claim 13 for quantitative measurement of blowing structures in prestressed panes, preferably in prestressed panes in buildings, in furniture, and devices or in means of transportation for travel on land, in the air, or on water, in particular side window panes and/or rear window panes of motor vehicles.

* * * * *